United States Patent [19]
Altscher et al.

[11] 3,939,227
[45] Feb. 17, 1976

[54] BIS(HYDROXY AND HALO ALKYL) ALKYL OR ARYL PHOSPHONATES

[75] Inventors: Siegfried Altscher, Monsey; Jagadish C. Goswami, New City, both of N.Y.

[73] Assignee: Stauffer Chemical Company, Westport, Conn.

[22] Filed: July 29, 1974

[21] Appl. No.: 492,562

[52] U.S. Cl............ 260/953; 260/2.5 AR; 260/977
[51] Int. Cl.² ....................... C07F 9/40; C08J 9/00
[58] Field of Search ................................... 260/953

[56] References Cited
UNITED STATES PATENTS

| | | | |
|---|---|---|---|
| 2,795,609 | 6/1957 | Jensen et al. | 260/953 X |
| 2,938,877 | 5/1960 | Mack et al. | 260/953 X |

*Primary Examiner*—Anton H. Sutto

[57] ABSTRACT

Reaction of halides of alkyl and aryl phosphonic acids of the formula $RP(O)X_2$, where R is an $C_1$-$C_{20}$ alkyl or aryl, e.g., phenyl, group or a halo-substituted $C_1$-$C_{20}$ alkyl group or aryl group, e.g., phenyl, and an epoxy group containing alcohol of the formula

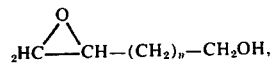

where $n$ is an integer from 1 to 8, e.g., glycidol, give a compound having the formula

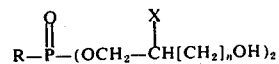

where R and n are as defined above which can be used as a flame retardant in polyurethane foams.

6 Claims, No Drawings

BIS(HYDROXY AND HALO ALKYL) ALKYL OR ARYL PHOSPHONATES

TECHNICAL DESCRIPTION OF THE INVENTION

The present invention relates to a diol containing both phosphorus and halogen and a process for forming said diol. The diol can be incorporated in a polyurethane foam formulation to confer flame retardancy on the polyurethane foam formed therefrom.

The diols of the present invention have the formula

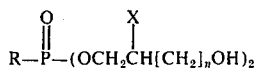

where X is halogen, e.g., chlorine, bromine or iodine and R is $C_1$-$C_{20}$ alkyl, aryl, e.g., phenyl, or halo-substituted $C_1$-$C_{20}$ alkyl or aryl. This compound is formed by the reaction of halides of alkyl or aryl phosphonic acids having the formula $RP(O)X_2$, where R and X are as defined above, with an epoxy group containing alcohol of the formula

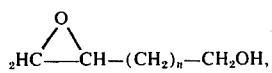

where $n$ is an integer from 1 to 8, such as glycidol. The molar ratio of such reactants is preferably 1:1 to 1:4, most preferably about 1:2. The reaction is best carried out in an inert chlorinated hydrocarbon solvent, such as methylene chloride, ethylene chloride and carbon tetrachloride, which will not react with the alkyl or aryl phosphonic dichloride. The phosphonic dihalide should be added to the solvent and alcohol by means of a controlled rate of addition, preferably dropwise at a temperature of below about 40°C. The time of addition should be between about 1 hour and 6 hours, most preferably about 3 hours. The reaction should be carried out under an inert atmosphere, e.g., nitrogen. The reaction mixture can be heated, e.g., to about 40°C.–80°C., after the addition has been performed to complete the reaction.

The product is a diol which can be readily dispersed in conventional polyols, e.g. polyether polyols, and which can be used in the fabrication of polyurethane foams. Persons of ordinary skill in the art are well able to devise suitable polyurethane foam formulations for use with the invention. Descriptions of the various reactants for such foam formulations are found in the following publications which are incorporated herein by reference: Kirk-Othmer Encyclopedia of Chemical Technology, "Foamed Plastics", Vol. 9, pp. 853–854 (1966), Saunders et al., Polyurethanes, Chemistry and Technology, Vols. I & II, Interscience Publishers (1963) and A. Cooper, Plastics Inst. (London) Trans. J., Vol. 29, p. 39 (1961). The product can be admixed with other components of the foam as well. When the product is blended, for example, with about ⅓ of its own weight of haloalkyl esters of phosphonic acid, e.g., tris(dibromopropyl phosphate), it produces a flame retardant foam having about 0.9–1% phosphorus, about 2.7% chloride and about 1.9% bromine.

The following Examples further illustrate the present invention:

EXAMPLE I

Into a 3-neck 500 ml. flask fitted with a stirrer condenser, funnel and a thermometer was charged the following materials:

| | |
|---|---|
| Methylene Chloride | 100g |
| Glycidol | 80g |

The thus charged flask was first cooled in an ice-bath (to approximately 3°C.) and then 90.3g. of chloromethyl phosphonic dichloride was added dropwise from the funnel keeping the reaction temperature below 40°C. The addition took approximately 3 hours. The reaction (including the addition of chloromethyl phosphonic dichloride) was carried out under an atmosphere of dry nitrogen gas. After the addition was complete, the reaction temperature was raised (by heating the flask in an oil bath) to 60°C. and the reaction was continued at this temperature for an additional hour. After the reaction was over, methylene chloride solvent was removed by applying vacuum, first at room temperature, followed by heating to 60°C. The product (152g) was a highly viscous material which could be readily dispersed in polyether polyol. The phosphorus and chlorine contents of the product are expected to be approximately 9.8% and 33%, respectively.

EXAMPLE II

This Example illustrates the preparation of a flame-retarding polyurethane foam from the reaction product (at 15 parts level) in conjunction with a haloalkyl ester of phosphoric acid flame retardant (5 parts level). The foam prepared from this combined 20 parts of flame-retarding additives/100g. of polyol passed the initial flammability (ASTM D-1692) as well as the dry heat aging (ASTM D-1564) tests. The formulation with this mixed additive is as follows:

| | |
|---|---|
| Thanol F-3002 polyol | 100.0g |
| Reaction Product | 15.0g |
| Tris(dibromopropyl) phosphate | 5.0g |
| Triethylamine | 0.2g |
| L-540 Silicon Surfactant | 0.8g |
| $H_2O$ | 4.0g |
| N-ethylmorpholine | 1.2g |
| A-1 catalyst | 1.0g |
| Stannous Octoate (50% in dioctyl phthalate) | 1.6g |
| Toluene diisocyanate | 56.0g |

Foam Characteristics
Foam rise and gelling good.

Density: Approximately 2 lbs/ft³

| | |
|---|---|
| Initial Flammability (ASTM D-1692): | Foam is self-extinguishing |
| Average Extinguishment Time ($T_{SE}$) | 42 seconds |
| Average Distance Burnt | 2.1 inches |
| Burning Rate | 3 inches/minute |
| Dry Heat Aging Test (ASTM D-1564): | Foam is self-extinguishing |
| Average Extinguishment Time ($T_{SE}$) | 43 seconds |
| Average Distance Burnt | 2.2 inches |
| Burning Rate | 3.1 inches/minute |

What is claimed:
1. Compounds of the formula

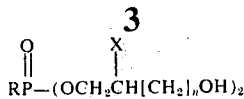

where *n* is an integer from 1 to 8, R is selected from the group consisting of $C_1$-$C_{20}$ alkyl, phenyl and halo- substituted $C_1$-$C_{20}$ alkyl and phenyl and X is halogen.

2. Compounds as set forth in claim 1 wherein R is —$CH_2Cl$.

3. Compounds as claimed in claim 1 wherein X is selected from the group consisting of chlorine, bromine and iodine.

4. Compounds as claimed in claim 1 wherein R is a $C_1$-$C_{20}$ alkyl group.

5. Compounds as claimed in claim 1 wherein R is a phenyl group.

6. Compounds as claimed in claim 1 wherein R is a halosubstituted $C_1$-$C_{20}$ alkyl group.

* * * * *